(12) United States Patent
Morrissey et al.

(10) Patent No.: US 9,290,729 B2
(45) Date of Patent: Mar. 22, 2016

(54) CONTAINER HAVING VORTEX BREAKER AND SYSTEM

(75) Inventors: Martin Morrissey, Beverly, MA (US); James E. Kelly, Jr., Melrose, MA (US); Dennis Wong, Dedham, MA (US); Steve Mello, Bradford, MA (US); Jean-Louis Weissenbach, Barr (FR)

(73) Assignee: EMD Millipore Corporation, Billerica, MA (US)

( * ) Notice: Subject to any disclaimer, the term of this patent is extended or adjusted under 35 U.S.C. 154(b) by 99 days.

(21) Appl. No.: 12/454,461

(22) Filed: May 18, 2009

(65) Prior Publication Data

US 2010/0012666 A1    Jan. 21, 2010

Related U.S. Application Data

(60) Provisional application No. 61/130,349, filed on May 30, 2008.

(51) Int. Cl.
| | |
|---|---|
| B65D 6/40 | (2006.01) |
| B01D 21/26 | (2006.01) |
| B65D 47/04 | (2006.01) |
| B01F 13/00 | (2006.01) |
| C12M 1/00 | (2006.01) |
| C12M 1/21 | (2006.01) |
| B01D 33/15 | (2006.01) |
| B01D 33/27 | (2006.01) |

(52) U.S. Cl.
CPC ............... *C12M 23/28* (2013.01); *C12M 23/26* (2013.01); *C12M 41/02* (2013.01)

(58) Field of Classification Search
CPC ............... B65D 47/043; B01F 2005/0025; B01F 13/0096; C12M 23/26; C12M 23/28; C12M 27/18; C12M 27/20; C12M 41/02; C12M 27/22
USPC ........................................ 220/601; 210/512.1
See application file for complete search history.

(56) References Cited

U.S. PATENT DOCUMENTS

| 969,997 A | 9/1910 | Thiem |
|---|---|---|
| 2,917,131 A | 12/1959 | Evans |
| 4,125,468 A | 11/1978 | Joh et al. |
| 4,394,966 A * | 7/1983 | Snyder et al. ............. 239/127 |
| 4,696,741 A | 9/1987 | Rahlwes |

(Continued)

FOREIGN PATENT DOCUMENTS

| EP | 0460804 | 12/1991 |
|---|---|---|
| FR | 2213904 A2 | 8/1974 |

(Continued)

OTHER PUBLICATIONS

International Search Report and Written Opinion received for PCT Patent Application No. PCT/US2009/003077, mailed on Apr. 9, 2010, 7 pages.

(Continued)

*Primary Examiner* — Fenn Mathew
*Assistant Examiner* — Andrew T Kirsch
(74) *Attorney, Agent, or Firm* — EMD Millipore Corporation

(57) ABSTRACT

A disposable container for fluid having an inlet and an outlet is provided. The container has a vortex breaker having a solid surface adapted to initially direct fluid away from the outlet and then through the outlet positioned adjacent the container outlet.

16 Claims, 2 Drawing Sheets

(56) References Cited

U.S. PATENT DOCUMENTS

| | | | |
|---|---|---|---|
| 4,885,089 A | | 12/1989 | Hankammer |
| 4,964,984 A | | 10/1990 | Reeder et al. |
| 4,987,922 A | * | 1/1991 | Andrepont et al. ........... 137/592 |
| 5,096,578 A | | 3/1992 | Strickland et al. |
| 5,209,765 A | * | 5/1993 | Kolpak et al. ................... 96/157 |
| 5,229,292 A | * | 7/1993 | Stock et al. .................. 424/93.2 |
| 6,335,191 B1 | | 1/2002 | Kiplinger et al. |
| 6,622,871 B2 | | 9/2003 | Gabele et al. |
| 6,638,426 B1 | | 10/2003 | Fritter et al. |
| 6,649,063 B2 | | 11/2003 | Brugger et al. |
| 6,739,456 B2 | | 5/2004 | Svoronos et al. |
| 6,827,238 B2 | | 12/2004 | Barker et al. |
| 6,983,899 B2 | * | 1/2006 | Melendez ...................... 239/548 |
| 2001/0051371 A1 | | 12/2001 | Kiplinger et al. |
| 2004/0062140 A1 | | 4/2004 | Cadogan et al. |
| 2004/0194751 A1 | | 10/2004 | Limbrunner et al. |
| 2004/0226879 A1 | | 11/2004 | Redding |
| 2004/0256325 A1 | * | 12/2004 | Frankiewicz et al. ......... 210/703 |

FOREIGN PATENT DOCUMENTS

| | | |
|---|---|---|
| FR | 2525919 A1 | 11/1983 |
| JP | 51-145646 U | 11/1976 |
| JP | 58-183298 U | 12/1983 |
| JP | 7-187282 A | 7/1995 |

OTHER PUBLICATIONS

International Preliminary Report on Patentability received for PCT Patent Application No. PCT/US2009/003077, issued on Nov. 30, 2010, 5 pages.

International Search Report and Written Opinion received for PCT Patent Application No. PCT/US2009/003075, mailed on Sep. 18, 2009, 8 pages.

International Preliminary Report on Patentability received for PCT Patent Application No. PCT/US2009/003075, issued on Nov. 30, 2010, 6 pages.

* cited by examiner

CONTAINER HAVING VORTEX BREAKER AND SYSTEM

CROSS-REFERENCED TO RELATED APPLICATIONS

This application claims the benefit of U.S. Provisional Patent Application No. 61/130,349, filed on May 30, 2008, the entire contents of which are incorporated by reference herein.

FIELD OF THE INVENTION

This invention relates to a disposable container having a vortex breaker at its outlet and to a system utilizing the container.

BACKGROUND OF THE INVENTION

Prior to the present invention, fluids have been processed in systems that utilize stainless steel containers. These containers are sterilized after use so that they can be reused. The sterilization procedures are expensive and cumbersome as well as being ineffectual at times.

In order to provide greater flexibility in manufacturing and reduce the time needed to effect valid regeneration, manufacturers have begun to utilize disposable sterilized bags that are used with each product batch. An example of use of these disposable bags is in a system for producing proteins by biological processing wherein the protein is derived from growing cells and then recovered. A problem occurs at the bag outlet where the fluid is removed from the bag. When the fluid is removed, one or more conical shaped vortices are formed from a conical column of gas present in the bag. This is undesirable since a vortex will cause mixing of the fluid with gas which results in undesirable foaming. A vortex will also entrain air into the protein filled fluid. This is undesirable since air can denature protein. Air entrainment into the flow stream also causes problems with processing equipment such as gages, sensors, pumps and filters.

Accordingly, it would be desirable to provide a disposable container for fluids having means for minimizing or preventing foaming at the container outlet.

SUMMARY OF THE INVENTION

A disposable container for a fluid having an inlet and an outlet is provided having a device for minimizing or preventing foaming of fluid at the outlet.

A system is also provided that utilizes the container with a unit operation down stream of the container such as a normal flow filtration (NFF) unit or the like whereby treated fluid is recovered. For example, the effluent from the container can be directed through clarification depth filters, pre-filters or microporous membrane filters. Examples of specific unit operations include clarification, buffer and media preparation and virus removal.

The outlet is provided with a vortex breaker comprising a solid surface that initially directs fluid away from the outlet. Openings are provided adjacent the solid surface which permits fluid to enter the outlet. The initial direction of fluid away from the outlet minimizes or prevents the formation of one or more vortices at the outlet.

DESCRIPTION OF SPECIFIC EMBODIMENTS

The disposable container of this invention is formed of monolayer or multilayer flexible walls formed of a polymeric composition such as polyethylene, including ultrahigh molecular weight polyethylene, linear low density polyethylene, low density or medium density polyethylene; polypropylene; ethylene vinyl acetate (EVOH); polyvinyl chloride (PVC); polyvinyl acetate (PVA); ethylene vinyl acetate copolymers (EVA copolymers); blends of various thermoplastics; coextrusions of different thermoplastics; multilayered laminates of different thermoplastics; or the like. By "different" it is meant to include different polymer types such as polyethylene layers with one or more layers of EVOH as well as the same polymer type but of different characteristics such as molecular weight linear or branched polymer of fillers and the like. Typically medical grade and preferably animal-free plastics are used. They generally are sterilizable such as by steam, ethylene oxide or radiation such as beta or gamma radiation. Most have good tensile strength, low gas transfer and are either transparent or at least translucent. The container is provided with an inlet, and an outlet. The outlet is provided with a vortex breaker positioned adjacent the outlet and secured to the inside surface of the container such as by heat sealing or with an adhesive. Optionally, the vortex breaker can be molded into the outlet structure. In a preferred embodiment, the disposable container is positioned within a solid support container for ease of filling and emptying the container of fluid.

Figure 1:
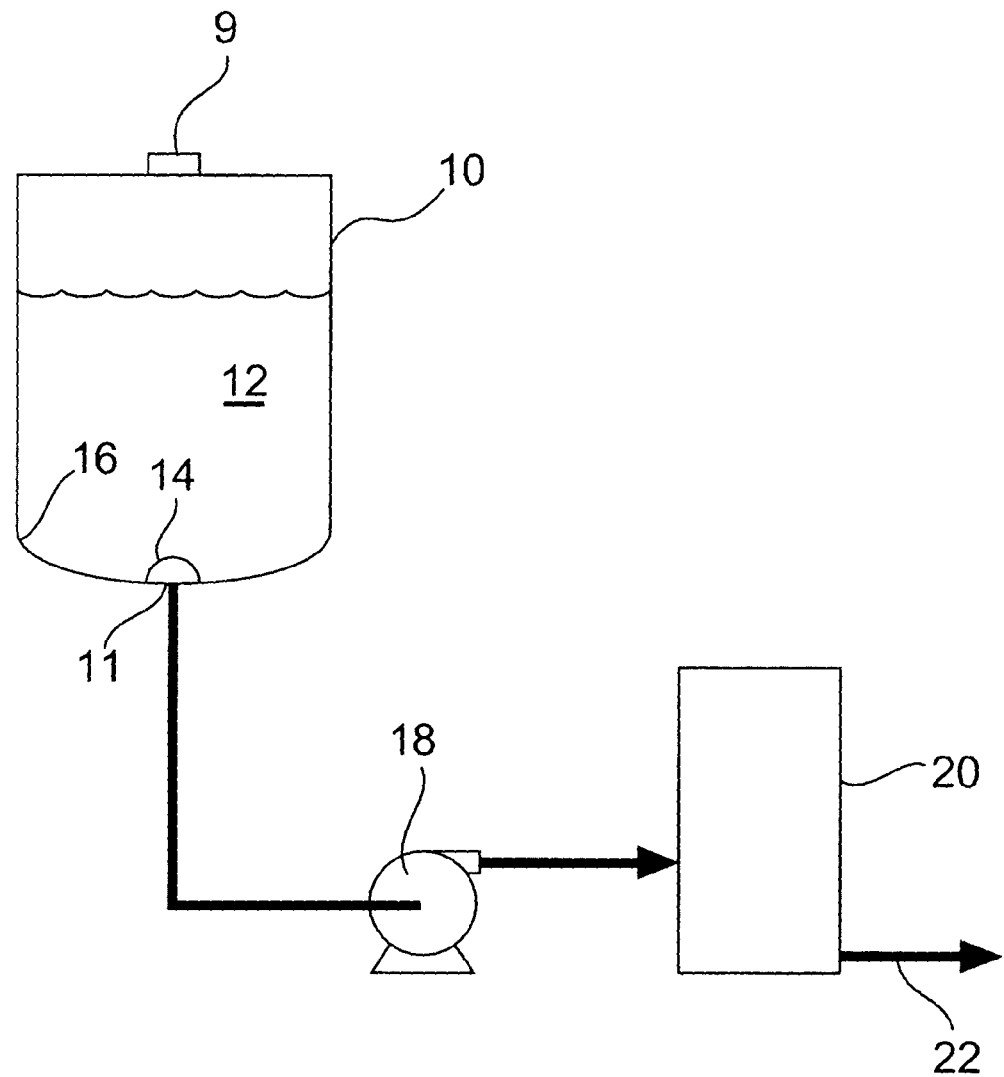
FIG. 1 is a schematic view of a system of this invention.

Referring to FIG. 1, the container of this invention 10 having inlet 9 and containing fluid 12 includes a vortex breaker 14 secured to the inner surface 16 of the container 10 at outlet 11. A pump 18 is provided to direct the fluid 12 through the outlet 11 to a downstream unit operation such as a filtration unit 20 as shown. An example of a process utilized with the system of this invention is the production of proteins derived from growing cells which are lysed to release cellular protein. The protein then is isolated by filtration to separate cell debris from the protein. The filtrate is directed through conduit 22 to a point of use or to be further treated.

Figure 2:
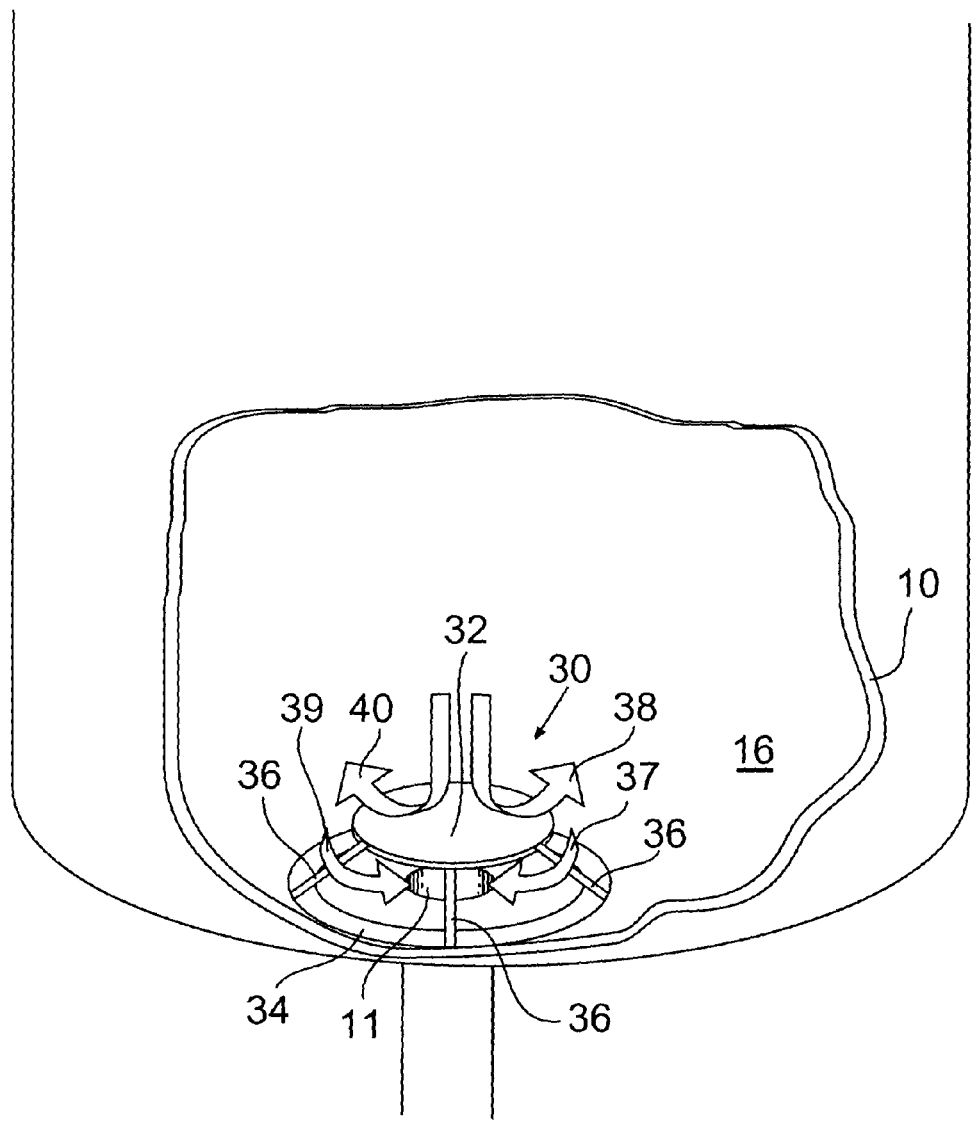
FIG. 2 is a perspective view of a vortex breaker positioned adjacent an outlet of the container of this invention.

Referring to FIG. 2, a vortex breaker 30 of this invention is shown. The vortex breaker comprises a solid surface 32 that can be any shape including circular, as shown or polygonal. The base 34 is sealed to the inner wall 16 of container 10. The vortex breaker 30 is positioned adjacent outlet 11. The solid surface 32 is supported by supports 36 attached to solid surface 32 and base 34. The vortex breaker 30 initially causes fluid to be directed away from outlet 11 as indicated by arrows 38 and 40 and then is directed to outlet 11 through the spaces between supports 36 as indicated by arrows 37 and 39. By operating with this vortex breaker, formation of vortices is minimized or prevented. The vortex breaker may also be formed as part of the outlet 11.

What is claimed:

1. A disposable container for a fluid comprising:
    a disposable container having a volume, the container being formed of polymeric flexible walls,
    an inlet through one of said walls,
    an outlet through one of said walls, and
    a vortex breaker, said vortex breaker being formed of a solid surface, a base and spaced apart solid supports between the solid surface and the base, the solid surface being secured to the base by the spaced apart solid supports, the base of the vortex breaker being secured to an inner surface of said container adjacent said outlet, wherein the base and the solid surface of the vortex breaker each have an outer diameter and the outer diameter of the base of the vortex breaker is greater than the outer diameter of the solid surface, the solid surface adapted to direct fluid initially away from said outlet and then through said outlet.

2. The container of claim 1 wherein the vortex breaker is formed as part of the outlet.

3. The container of claim 1 wherein the solid surface has a circular shape.

4. The container of claim 1 wherein the solid surface has a polygonal shape.

5. A fluid processing system which comprises:
a disposable container for a fluid comprising: a disposable container having a volume, the container being formed of polymeric flexible walls, an inlet through one of said walls, an outlet through one of said walls, and a vortex breaker, said vortex breaker being formed of a solid surface, a base and spaced apart solid supports between the solid surface and the base, the solid surface being secured to the base by the spaced apart solid supports, the base of the vortex breaker being secured to an inner surface of said container adjacent said outlet, wherein the base and the solid surface of the vortex breaker each have an outer diameter and the outer diameter of the base of the vortex breaker is greater than the outer diameter of the solid surface, the solid surface adapted to direct fluid initially away from said outlet and then through said outlet,
a unit operation downstream of the container, and
one or more conduits to affect flow from said container to said unit operation.

6. The system of claim 5, wherein the unit operation is clarification, buffer preparation, media preparation, or virus removal.

7. A system for transferring a protein containing liquid comprising: a disposable container having a volume, the container being formed of:
polymeric flexible walls,
an inlet through one of said walls,
an outlet through one of said walls, the outlet being in fluid communication with a unit operation downstream of the container, and
a vortex breaker, said vortex breaker being formed of a solid surface, a base and spaced apart solid supports between the solid surface and the base, the solid surface being secured to the base by the spaced apart solid supports, the base of the vortex breaker being secured to an inner surface of said container adjacent said outlet, wherein the base and the solid surface of the vortex breaker each have an outer diameter and the outer diameter of the base of the vortex breaker is greater than the outer diameter of the solid surface, the solid surface adapted to direct fluid initially away from said outlet and then through said outlet to the unit operation.

8. The system of claim 7 wherein the unit operation is a normal flow filtration unit.

9. The system of claim 7 wherein the unit operation is a normal flow filtration unit selected from the group consisting of clarification depth filters, pre-filters and microporous membrane filters.

10. The system of claim 7 wherein the solid surface has a circular shape.

11. The system of claim 7 wherein the solid surface has a polygonal shape.

12. The system of claim 7, wherein the unit operation is clarification, buffer preparation, media preparation, or virus removal.

13. A method of transferring a protein containing liquid from a container to a unit operation comprising:
a) providing a disposable container having a volume, the container being formed of polymeric flexible walls, the container having an inlet through one of said walls, an outlet through one of said walls, the outlet being in fluid communication with a unit operation downstream of the container and a vortex breaker, said vortex breaker being formed of a solid surface, a base and spaced apart solid supports between the solid surface and the base, the solid surface being secured to the base by the spaced apart solid supports, the base of the vortex breaker being secured to an inner surface of said container, adjacent said outlet, wherein the base and the solid surface of the vortex breaker each have an outer diameter and the outer diameter of the base of the vortex breaker is greater than the outer diameter of the solid surface, the solid surface adapted to direct fluid initially away from said outlet and then through said outlet and a pump between the outlet and the unit operation,
b) having a protein containing liquid in the container,
c) pumping the protein containing liquid through the vortex breaker and the outlet to the unit operation wherein the vortex breaker minimizes or inhibits the formation of one or more vortices at the outlet, and
d) recovering the liquid from the unit operation.

14. The method of claim 13 wherein the solid surface has a circular shape.

15. The method of claim 13, wherein the unit operation is clarification, buffer preparation, media preparation, or virus removal.

16. The method of claim 13 wherein the solid surface has a polygonal shape.

* * * * *